US006534541B1

(12) United States Patent
Goldblum

(10) Patent No.: US 6,534,541 B1
(45) Date of Patent: Mar. 18, 2003

(54) TREATMENT OF OCULAR DISORDERS

(75) Inventor: David Goldblum, New York, NY (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/686,025

(22) Filed: Oct. 11, 2000

(30) Foreign Application Priority Data

Oct. 19, 1999 (EP) .............................. 99120678

(51) Int. Cl.[7] ...................... A61K 31/27; C07C 271/00
(52) U.S. Cl. .................. 514/476; 514/478; 514/490; 560/136
(58) Field of Search .................. 560/136; 514/476, 514/478, 490

(56) References Cited

U.S. PATENT DOCUMENTS

| 4,900,748 A | | 2/1990 | Brossi et al. ............... 514/411 |
| 4,948,807 A | * | 8/1990 | Rosin et al. |
| 5,602,176 A | * | 2/1997 | Enz |

FOREIGN PATENT DOCUMENTS

| EP | 0 193 926 | | 9/1986 |
| FR | 2 611 707 | | 9/1988 |
| WO | 93/05779 | | 4/1993 |
| WO | 93/06105 | | 4/1993 |
| WO | WO 97/23226 A1 | * | 7/1997 |

OTHER PUBLICATIONS

Sneader, Walter; "From Ordeal Poison to Alzheimer's Therapy," Drug News Perspect., vol. 12(7), pp. 433–437 (1999).
European Search Report.
Goldblum et al., "Topical Rivastigmine, a selective Acetylcholinesterase Inhibitor, Lowers Intraocular Pressure in Rabbits", Journal of Ocular Pharmacology and Therapeutics, vol. 16, No. 1, pp. 29–35, (Feb. 2000).
Sim, Alasdair, "Rivastigmine: a review", Hospital Medicine, vol. 60, pp. 731–735, (1999).

* cited by examiner

Primary Examiner—Johann Richter
Assistant Examiner—Paul A. Zucker
(74) Attorney, Agent, or Firm—David E. Wildman

(57) ABSTRACT

The present invention is in particular related to the use of rivastigmine in the manufacture of a medicament for the treatment of ocular disorders.

5 Claims, No Drawings

TREATMENT OF OCULAR DISORDERS

This invention is in particular related to the use of rivastigmine in the manufacture of a medicament for the treatment of ocular disorders selected from glaucoma and neurodegenerative disease conditions of the retina and the optic nerve.

The term glaucoma includes symptoms of the eye which are especially to be attributed to increased intraocular pressure. Frequently, an obstruction to drainage of the aqueous humour leads to an increase in the intraocular pressure. Chronically raised intraocular pressure has a harmful effect on the optic nerve and the retina, which can terminally lead to blindness. Accordingly, for the treatment of glaucoma, active ingredients are used which are typically able to reduce the intraocular pressure (IOP). For example, increased IOP be treated with certain β-adrenoceptor blockers.

More recently, the phenomenon of so-called normal tension glaucoma ("low tension" or "normal tension glaucoma" is used synonymously) has now been clinically established in ophthalmology [J. Flammer, Fortschr. Ophthalmol. 87, 187(1990)]. Normal tension glaucoma is characterized by an intraocular pressure which is typically in the normal range, i.e. is not increased, but in which the optic disc (papilla nervi optici) is pathologically excavated and the field of vision is impaired. The pathogenetic factors are especially circulatory problems in the ocular blood vessels, which may be caused e.g. by atherosclerosis, hypotension, orthostasis, functional vasospasms and neurodegenerative factors.

It has now surprisingly been found that rivastigmine, its racemate, its analogs and/or its pharmaceutically acceptable salts are highly effective in the treatment of glaucoma and disorders of neurological pathogenesis (neurodegeneration), such as normal tension glaucoma.

Accordingly, a first aspect of the present invention is related to the use of a compound of formula (I),

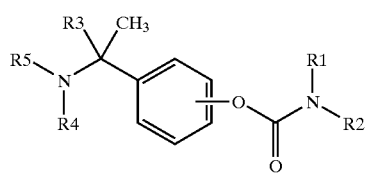

(I)

wherein
R1 is hydrogen, lower alkyl, cyclohexyl, allyl or benzyl,
R2 is hydrogen, methyl, ethyl or propyl or
R1 and R2 together with the nitrogen to which they are attached form a morpholino or piperidino radical,
R3 is hydrogen or lower alkyl,
R4 and R5 are the same or different and each is a lower alkyl, and the dialkylaminoalkyl group is in the meta, ortho or para position,
in free base or pharmaceutically acceptable acid addition salt form,
in the preparation of a pharmaceutical composition for the treatment of an ocular disorder selected from the group consisting of glaucoma, normal tension glaucoma and neurodegenerative disease conditions of the retina and the optic nerve.

In a preferred embodiment the dialkylaminoalkyl group is in the meta position.

A more preferred compound in accordance to formula (I) is racemic N-ethyl-3-[(1-diethylamino)-ethyl]-N-methyl-phenyl-carbamate free base and/or acid addition salt.

An even more preferred compound in accordance to formula (I) is (S)-N-ethyl-3-[(1-diethylamino)-ethyl]-N-methyl-phenyl-carbamate free base and/or acid addition salt.

A preferred acid addition salt is derived from tartraric acid.

A highly preferred compound in accordance to formula (II) is (S)-N-ethyl-3-[(1-diethylamino)-ethyl]-N-methyl-phenyl-carbamate hydrogen tartrate (rivastigmine).

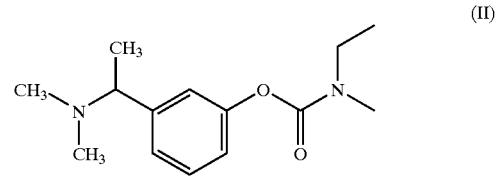

(II)

This invention is preferably related to the treatment of normal tension glaucoma and neurodegenerative disease conditions of the retina and the optic nerve, and even more preferred to neurodegenerative disease conditions of the retina and the optic nerve.

A further aspect of the present invention is a method of treating an ocular disorder, which disorder is selected from the group consisting of glaucoma, normal tension glaucoma and neurodegenerative disease conditions of the retina and the optic nerve, which method comprises the repeated administration of a pharmaceutically effective amount of a compound of formula (I), to an individual in need of such treatment,

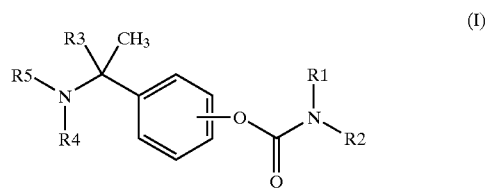

(I)

wherein
R1 is hydrogen, lower alkyl, cyclohexyl, allyl or benzyl,
R2 is hydrogen, methyl, ethyl or propyl or
R1 and R2 together with the nitrogen to which they are attached form a morpholino or piperidino radical,
R3 is hydrogen or lower alkyl,
R4 and R5 are the same or different and each is a lower alkyl, and the dialkylaminoalkyl group is in the meta, ortho or para position,
in free base or pharmaceutically acceptable acid addition salt form.

A preferred mode of administering a compound of the present invention is the topical, and more preferably the topical ocular administration.

A preferred group of individuals are human beings.

The term repeated administration refers in particular a weekly and more preferably to a daily administration, wherein the active is administered in regular intervals from one to ten times, more preferably from one to six times, and even more preferably from one to three times.

For the purposes of the present invention, the term "lower" in connection with radicals and compounds, unless defined otherwise, denotes, in particular, radicals or compounds having up to 8 carbon atoms, preferably up to 4 carbon atoms.

Accordingly, lower alkyl has up to 8 carbon atoms, and can be straight-chain or branched, preferably up to 4 carbon atoms, and is, for example; methyl, ethyl, propyl, iso-propyl, butyl, sec-butyl, tert-butyl, pentyl, hexyl or isohexyl.

Alkyl has up to 18 carbon atoms and can be straight-chain or branched. Suitable examples are octadecyl, undecyl, octyl, hexyl, pentyl, butyl, propyl, ethyl, and the like.

MATERIALS AND METHODS

1. Animals

Male and female adult brown burgundy rabbits (2.6–4.4 kg) are used in this study. Animals are kept in individual cages under well-defined and standardized conditions (humidity and temperature controlled room, 13 h light/11 h dark cycle) with standard dry food and water adlibitum. All animals are accustomed to the procedure of IOP measurement by only those animals that have stable records are included in the study. All experiments are conducted in accordance with the ARVO resolution for the use of animals in ophthalmic and vision research and are approved by the Federal and Local Ethical and Agricultural Committees.

2. Drugs

Compounds in accordance to formula (I) indicated above and in particular (S)-Nethyl-3-[(1-diethylamino)-ethyl]-N-methyl-phenyl-carbamate.

Topical anaesthesia of the cornea is induced with Novocaine 0.2% (Inselspital Pharmacy) eye drops.

Solutions of a test drug are freshly prepared before each experiment by dissolution in sterile balanced salt solution (BSS) (Alcon Pharmaceuticals Ltd, Forth Worth, Tex., USA) at the required concentrations under sterile conditions. One 50-$\mu$L drop of the test solution is applied topically to the right eye whereas the contralateral eye receives the carrier BSS only.

3. IOP Measurements

IOP is measured with a TonoPen XL (Mentor, Norvel, Mass.), the device being calibrated daily according to the manufacturer's instructions. The first measurement result with a coefficient of variation displayed <5% is noted. Less than 5% of the measurements are repeated until the coefficient of variation displayed is <5%. Corneas are anaesthetized by topical application of a 50-$\mu$L drop of 0,2% Novocaine prior to each IOP measurement.

Measurements are always initiated at the same time (8 a.m.), a sufficient recovery period of at least 7 days is provided for the animals between the experiments. Control readings are taken 10 minutes before instillation of the test drug to the right eye and of the vehicle to the left one. IOP is recorded at 1-hour intervals for the ensuing 8 hours. Baseline measurements are likewise performed hourly in all animals prior to treatment, for monitoring of diurnal rhythms. (9)

4. Pupil Diameter

Pupil diameter is measured horizontally in both eyes using a pupil gauge closely applied to the cornea under diffuse illumination conditions.

5. Slit-Lamp Examination

Slit-lamp biomicroscopy is performed by a trained ophthalmologist before drug administration and 4 and 8 hours thereafter. Eyes are controlled for conjunctival redness and discharge, for integrity of the corneal epithelium and for the absence or presence of flare (protein in the anterior chamber being an indication of blood aqueous barrier breakdown).

6. Statistical Analysis

Data are analyzed according to the Mann-Whitney U-test. IOP values recorded before and after application of Rivastigmine or the drug vehicle are compared in the same eye, differences with a first order error of $P<0.05$ being considered as statistically significant.

Results

Rivastigmine lowers the IOP significantly in the treated eye. Maximal mean decreases in IOP are time-staggered according to the concentration of the drug solution used, occurring 1, 3, and 5 hours after application of 5% (3.5±1.2 mm Hg), 2% (2.2±0.8 mm Hg), and 1% rivastigmine (2.6±1.2 mm Hg), respectively. After administration of the 1% rivastigmine solution the longest significant IOP-lowering effect is observed during 5 hours in the treated eyes (Table 1A). In untreated eyes, maximal mean decreases in IOP are likewise time-staggered, occurring 1, 3, and 4 hours after application of 5%, 2%, and 1% rivastigmine, respectively, to the contralateral ones. However, only the effect induced by 5% rivastigmine is significant (Table 1 B). Overall, in the treated and untreated eyes, the maximal IOP decrease occurs 1 hour after administration of the 5% drug solution.

An insignificant miotic pupil reaction is observed in some drug-treated eyes. No signs of rivastigmine-related local toxicity are manifested.

TABLE 1A

Right eye data (treated)

| | Time (hrs) | | | | | | | | |
|---|---|---|---|---|---|---|---|---|---|
| | 0 | 1 | 2 | 3 | 4 | 5 | 6 | 7 | 8 |
| IOP (mm) Control | 12.1 | 13.8 | 14.0 | 12.3 | 12.3 | 13.0 | 12.9 | 11.5 | 13.0 |
| 1% Rivastigmine | 12.3 | 12.0 | 11.2 | 10.8 | 10.5 | 10.1 | 11.1 | 11.5 | 11.6 |
| 2% Rivastigmine | 11.5 | 11.5 | 11.0 | 9.2 | 10.8 | 11.5 | 11.1 | 10.8 | 12.0 |
| 5% Rivastigmine | 13.7 | 10.0 | 11.1 | 10.8 | 10.5 | 12.9 | 12.5 | 14.0 | 11.8 |

TABLE 1B

Left eye data (untreated)

| | Time (hrs) | | | | | | | | |
|---|---|---|---|---|---|---|---|---|---|
| | 0 | 1 | 2 | 3 | 4 | 5 | 6 | 7 | 8 |
| IOP (mm) Control | 12.2 | 13.4 | 13.2 | 12.0 | 12.8 | 13.9 | 13.5 | 12.1 | 14.0 |
| 1% Rivastigmine | 12.0 | 11.6 | 11.2 | 11.1 | 10.2 | 11.0 | 10.7 | 11.1 | 11.4 |

TABLE 1B-continued

| | Left eye data (untreated) | | | | | | | | |
|---|---|---|---|---|---|---|---|---|---|
| | Time (hrs) | | | | | | | | |
| | 0 | 1 | 2 | 3 | 4 | 5 | 6 | 7 | 8 |
| 2% Rivastigmine | 11.2 | 11.9 | 11.2 | 10.2 | 12.3 | 11.5 | 11.2 | 11.0 | 13.0 |
| 5% Rivastigmine | 13.4 | 10.7 | 11.5 | 11.3 | 11.9 | 13.2 | 12.5 | 13.3 | 13.0 |

The above tables 1A and 1B exhibit baseline measurements (positive SD) and mean IOP measurements recorded after topical application of a single 50-µL drop of 1% (n=8) (negative SD), 2% (n=4) and 5% (n=6) rivastigmine to the right eyes (A), and of a similar volume of the drug vehicle to the left ones (B), of normotensive adult rabbits. In the drug-treated group, maximal effects occur after 1 hour (5% rivastigmine), 3 hours (2% rivastigmine) and 5 hours (1% rivastigmine). In the untreated eyes, maximal IOP-reductions occur 1,3 and 4 hours after administration of 5%, 2% and 1% rivastigmine, respectively, to the partner ones. (**P<0.05)

The neuroprotective effect of rivastigmine—after topical application—in addition to its well-tolerated ocular hypotensive effect makes it a compound of choice for the treatment of normotensive glaucoma.

What is claimed is:

1. A method of decreasing intraocular pressure in a subject in need of such treatment comprising:
   repeatedly topically administering to the eye of a subject in need of treatment an amount effective to decrease intraocular pressure in said eye of said subject of a compound with the formula

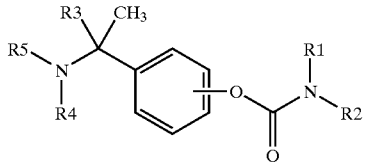

wherein
R1 is hydrogen, lower alkyl, cyclohexyl, allyl, or benzyl;
R2 is hydrogen, methyl, ethyl, or propyl; or
wherein R1 and R2 together with the nitrogen to which they are attached form a morpholino or piperidino radical;
R3 is hydrogen or lower alkyl;
R4 and R5 are, independently, lower alkyl;
wherein the

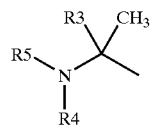

group is in the meta, ortho, or para position relative to the carbamate group;
or a pharmaceutically acceptable acid addition salt thereof.

2. The method of claim 1 wherein the

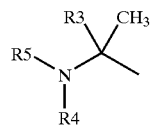

group is in the meta position relative to the carbamate group.

3. The method of claim 1, wherein the compound is racemic N-ethyl-N-methyl-3-[(1-dimethylamino)ethyl]-phenyl carbamate free base or an acid addition salt thereof.

4. The method of claim 1, wherein the compound is (S)-N-ethyl-N-methyl-3-[(1-dimethylamino)ethyl]-phenyl carbamate free base or an acid addition salt thereof.

5. The method of claim 1, wherein the compound is (S)-N-ethyl-N-methyl-3-[(1-dimethylamino)ethyl]-phenyl carbamate hydrogen (2R,3R)-tartrate.

* * * * *